United States Patent [19]

Sekura et al.

[11] Patent Number: 5,338,670
[45] Date of Patent: Aug. 16, 1994

[54] PRODUCTION OF BORDETELLA PERTUSSIS TOXIN WITH A LOW CONCENTRATION OF IRON

[75] Inventors: Ronald D. Sekura; Yan-Ling Zhang; Joseph Shiloach, all of Rockville, Md.

[73] Assignee: The United States of America as represented by the Department of Health and Human Services, Washington, D.C.

[21] Appl. No.: 989,908

[22] Filed: Dec. 11, 1992

Related U.S. Application Data

[63] Continuation of Ser. No. 504,022, Apr. 4, 1990, abandoned, which is a continuation of Ser. No. 338,459, Apr. 17, 1989, abandoned, which is a continuation of Ser. No. 889,621, Jul. 28, 1986, abandoned.

[51] Int. Cl.$^5$ .............................................. C12P 21/00
[52] U.S. Cl. .................. 435/71.3; 435/252.1; 435/244; 435/246; 435/822
[58] Field of Search ............... 435/68.1, 71.3, 244, 435/252.1, 246, 812, 813, 818, 822; 424/93 R

[56] References Cited

U.S. PATENT DOCUMENTS 2,822,319  8/1954  Monod .............................. 435/813
4,687,738  8/1987  Ginnaga et al. ...................... 435/68

OTHER PUBLICATIONS

Staimer, D. W. et al., "A Simple Chemically Defined Medium for the Production of Phase I" *Bordatella Petrussis, J. General Microbiology*, 63:211–220, 1971.
Armstrong, S. K. et al., "Effects of Iron Starvation on *Bordatella Petrussis*", Abstracts of the Annual Meeting of The American Society for Microbiology, Mar. 4–9, 1984.
Sekura, et al., (1983), J. Biol. Chem., 258:23, pp. 14647–14651, "Pertussis Toxin, Affinity Purification of a new ADP-Ribosyltransferase".
Sekura, et al., (1985), Methods of Enzymology, 109, p. 556 –"ADP-Ribosylation of Membrane Components by Pertussis and Cholera Toxin".

*Primary Examiner*—Marian Knode
*Attorney, Agent, or Firm*—Birch, Stewart, Kolasch & Birch

[57] ABSTRACT

A fermentation level cultivation of *Bordetella pertussis* bacteria on commercial scale is described. The critical factors in large scale cultivation of the bacteria are the presence of an antifoam agent and maintaining proper oxygen level and iron content in the culture medium. Pertussis toxin produced by the bacteria parallels the rate of growth of the bacteria.

6 Claims, 1 Drawing Sheet

PRODUCTION OF BORDETELLA PERTUSSIS TOXIN WITH A LOW CONCENTRATION OF IRON

This application is a continuation of application Ser. No. 07/504,022, filed on Apr. 4, 1990, now abandoned, which is a continuation of application Ser. No. 07/338,459, filed Apr. 17, 1989, now abandoned, which is a continuation of application Ser. No. 06/889,621, filed Jul. 28, 1986, which is abandoned.

BACKGROUND OF THE INVENTION

1. Technical Field

The present invention is related to a method of culturing *Bordetella pertussis* (*B. pertussis*) on a large scale. More particularly, the present invention is related to a method of fermentation level cultivation of *B. pertussis* concurrently producing pertussis toxin.

2. State of the Art

Pertussis toxin is one of the various components produced by virulent *B. pertussis*, the microorganism that causes whooping cough. This toxin is a major protective antigen against whooping cough. Other components of interest produced by *B. pertussis* are filamentous hemagglutinin, heat labile toxin, adenylate cyclase and the like which may also play important role as protective antigens. Large scale production of these components which are useful as diagnostic or chemical reagents and in the preparation of vaccines requires large scale cultivation of the microorganism.

*Bordetella pertussis* is a fastidious organism which has proved difficult to grow in large fermentors. Current methods for the culture of *B. pertussis* employ cultivation in stationary culture or in fermentors. Growth in stationary culture is labor intensive while cultivation on a fermentation scale requires vortex stirring and surface aeration. As a result, the effective volume of the fermentor is reduced and modification of the fermentor for growth of pertussis is often necessary, for example the baffles must be removed. Furthermore, the quantities of pertussis toxin produced during fermentation under these conditions are variable and often low.

SUMMARY OF INVENTION

It is, therefore, an object of the present invention to provide a method of cultivating *B. pertussis* in commercial scale fermentors under conditions which allow full utilization of the fermentor capacity.

It is a further object of the present invention to provide a method of producing pertussis bacteria and pertussis toxin in high yields.

Other objects and advantages would become evident as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

Figure 1:
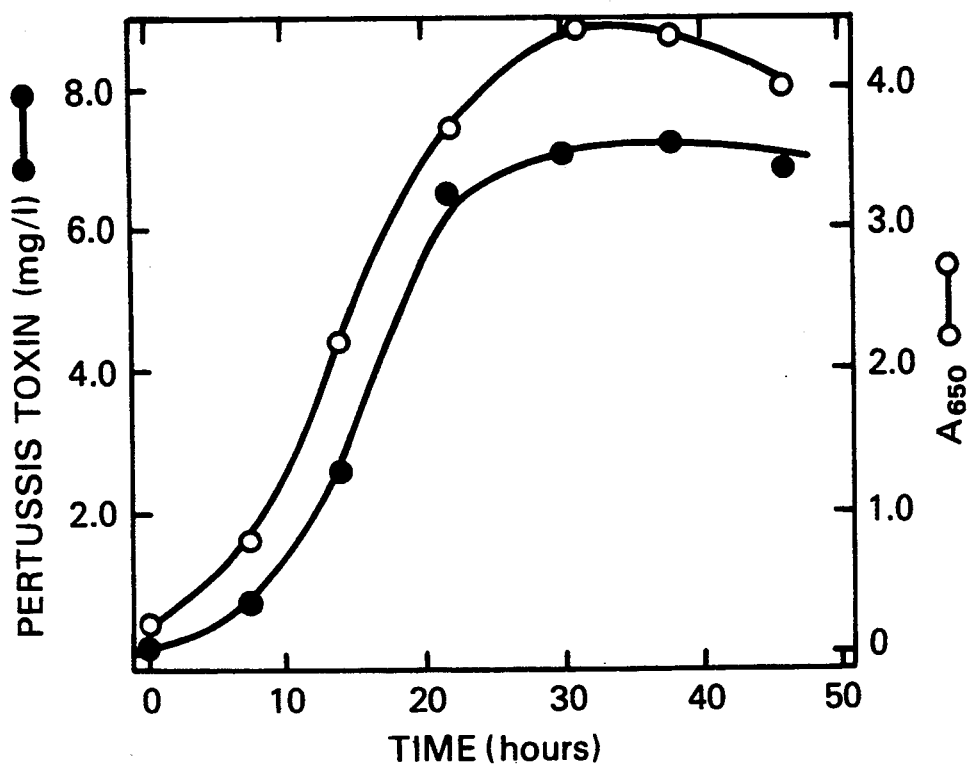
FIG. 1 illustrates *B. pertussis* cultivation and production capacity for pertussis toxin in a 100 liter fermentor. *B. pertussis*, strain CS, was cultivated in the fermentor. Samples were withdrawn during fermentation and their $A_{650}$ (○) and pertussis toxin concentration, as measured by ELISA (●) were determined.

The above and other objects and advantages of the present invention are achieved by a method of cultivating *B. pertussis* comprising the steps of:

(a) charging a fermentor of commercial scale capacity with a sterilized first medium capable of supporting growth of *Bordetella pertussis* and concomitant production of pertussis toxin;

(b) inoculating the first medium with a culture of *Bordetella pertussis* bacteria grown in a second culture medium containing growth promoting amount of an iron salt;

(c) cultivating the bacteria in agitated submerged culture at about 36° C. in the presence of an antifoam agent and dissolved oxygen at about 40% saturation level; and (d) maintaining said level of oxygen saturation in the culture medium by pure oxygen or air enriched with oxygen.

The term "commercial scale" or "large scale" fermentors as used herein means fermentors of such capacities as about 4 liters to 100 liters or larger.

Unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

A major problem encountered in attempting cultivation of *Bordetella pertussis* in submerged culture with bottom aeration is the tendency of bacteria to accumulate at the surface of the fermentation vessel as a pellicle which removes bacteria from submerged culture and results in the cessation of bacterial growth. Three critical factors discovered in successfully cultivating *B. pertussis* in accordance with the present invention are (1) incorporation of an antifoam agent; (2) controlling aeration by using pure $O_2$ or oxygen-enriched air; and (3) regulating iron content in the medium.

During early stages of cultivation when cell density is low and when oxygen requirements are not high, the tendency for pellicle formation can be effectively controlled by introduction of an appropriate anti-foam agent in the culture medium. As the demand for oxygen increases with increased cell density, anti-foam does not sufficiently control the problem. Instead it was found that reduction in the volume of gas entering the fermentor can effectively block pellicle formation. This can be achieved with maintenance of appropriate oxygen saturation by using oxygen rather than air for aeration. Implementation of these two measures has resulted in the ability to consistently cultivate *Bordetella pertussis* in fermentors of different sizes (4 liter to 100 liter) with good yield of bacterial growth. The methods as described herein are applicable to even larger fermentors.

The yield of pertussis toxin from bacteria grown in submerged culture can be variable. One of the factors affecting this variability has been discovered to be the iron content of the media. While high iron content supports greater bacterial Growth, it suppresses the production of pertussis toxin. By adjusting the iron content of modified Stainer-Scholte media as described by Hewlett et al, 1976, *J. Bacteriol.* 127:890, to 10% of the recommended concentration. Changing for example from about 10 mg FeSO$_4$-7H$_2$O per liter to about 1.0 mg per liter, the production of pertussis toxin is optimized.

The Effect of Antifoam and Aeration

In choosing an appropriate anti-foam for use in the cultivation of *Bordetella pertussis*, a study was conducted examining the effect of several of these materials on growth of the organism and on the level of pertussis toxin production (Table I). In Experiment 1 it was found that Antifoam C (30% polydimethylsiloxane and silica aerogel with 1.6% methylcellulose and 0.75% sorbic acid in water) was nontoxic to the bacteria and did not interfere with the production of pertussis toxin. Experiment 2 showed that anti-foam C could be included in media at concentrations of up to 1.0 ml per liter without adversely effecting growth or toxin production. For fermentation level cultivation, anti-foam C at a concentration of 0.5 ml per liter media was found to be adequate. However, as is clear, any anti-foam which does not affect the bacterial growth and toxin production, can, of course be employed.

To achieve optimal growth of the organism, aeration was achieved by introducing pure oxygen into the fermentor at a flow rate not exceeding about 8% of the fermentor volume per min. Regulation of dissolved oxygen at about 40% saturation resulted in a net gas input that did not cause pellicle formation when appropriate levels of anti-foam were present.

TABLE I

The effect of anti-foam on the growth of *Bordetella pertussis* and on the production of pertussis toxin.

| Experiment | Additions | A650 | Toxin (ug/ml) |
|---|---|---|---|
| 1 | none | 2.54 | 0.87 |
| | Anti-foam AF (0.02 g/200 ml) | 0.07 | 0 |
| | Anti-foam C | 2.45 | 0.94 |
| 2 | none | 1.22 | 0.49 |
| | Anti-foam C (0.02 g/200 ml) | 1.02 | 0.25 |
| | Anti-foam C (0.1 g/200 ml) | 1.24 | 0.52 |
| | Anti-foam C (0.2 g/200 ml) | 1.11 | 0.42 |

Bacteria were cultivated in 500 ml flasks containing 200 ml of Stainer-Scholte medium with the indicated additions. After incubation for 24 hr at 36° C., samples were taken for determination of bacterial growth (A-650) and pertussis toxin. Pertussis toxin concentration was determined by ELISA.

The Effect of Iron Content

Although any suitable source of iron can be utilized, ferrous sulfate is preferred. The level of ferrous sulfate included in modified Stainer-Scholte medium affects both the Growth of *Bordetella pertussis* and the level of pertussis toxin production (Table II). Experiment 1, where the input of iron into the culture is limited to the amount of iron introduced through the addition of 10% inoculum, shows that reduction of iron content leads to nearly a two fold increase in pertussis toxin production. Experiment 2 confirms this observation and additionally demonstrates that total exclusion of iron leads to suppressed bacterial growth with concomitant reduction of pertussis toxin production. For these reasons iron content during cultivation is maintained at about 10% of the levels in Stainer-Scholte medium and is limited to the material introduced with the inoculum.

TABLE II

The effect of medium iron content on the growth of *Bordetella pertussis* and on the production of pertussis toxin.

| | Iron | | | |
|---|---|---|---|---|
| Experiment | Inoculum | Culture | A-650 | Toxin (ug/ml) |
| 1 | + | + | 3.02 | 0.34 |
| | + | − | 2.52 | 0.67 |
| 2 | + | + | 3.47 | 0.25 |
| | + | − | 2.64 | 0.72 |
| | − | − | 2.05 | 0.50 |
| | − | −, Chelex | 1.64 | 0.36 |

*Bordetella pertussis* inoculla were cultivated in Stainer-Scholte, media with (+) or without (−) ferrous sulfate as indicated. Inoculla thus prepared were used to inoculate culture flasks containing complete medium (+), medium deficient in iron (−) or medium treated with Chelex. Cultivation was performed in 500 ml flasks containing 180 ml of medium; in each instance a 20 ml inoculum was used. After cultivation for 24 hr at 36 C samples were withdrawn and growth was determined by A-650. Pertussis toxin concentration was determined by ELISA.

Fermentation Level Cultivation

The method described herein has been employed successfully with several strains of *Bordetella pertussis*, including strains CS and 165, and is readily applicable to other strains. Innoculum for fermentation growth of the organism is prepared by passage of lyophilized stock cultures of bacteria on Bordet-Gengou blood agar plates. The Growth from these plates is used to inoculate culture flasks containing Stainer-Scholte medium containing suitable quantity of ferrous sulfate. Liquid cultures are expanded until an inoculum equal to 10% of the desired fermentation volume is achieved.

The method employed for cultivation of *Bordetella pertussis* in a 100 liter fermentor is now presented as an example. The fermentor is charged with 90 l of heat sterilized media containing: monosodium 1-glutamate (965 g), sodium chloride (225 g), potassium phosphate, monobasic (45 g), potassium chloride (18 g), magnesium chloride, hexahydrate (18 g), calcium chloride (1.8 g), 1-proline (21.6 g), Tris (21.6 g), and anti-foam C (45 ml) adjusted to pH 7.4 with HCl. At the time of innoculation, 1.0 l of filter sterilized supplement containing: 1-cystine (4.0 g, dissolved in 120 ml 1M HCl), ascorbic acid (2.0 g), niacin (0.4 g), and glutathione-reduced (10 g), is added. The fermentor is inoculated with bacterial growth (A$_{650}$ between about 2.0 and 3.0) from about six 1.3 liter cultures of *B. pertussis* grown on complete Stainer-Scholte medium containing ferrous sulfate at about 10 mg/liter. *B. pertussis* is then grown in submerged culture at about 36° C. Agitation, with a turbine impeller (ratio of diameter to width of about 0.3) is maintained at about 250 rpm throughout the run. The dissolved oxygen concentration is maintained at about 40% saturation by supplying pure oxygen through a dissolved oxygen controller and via a ring sparget underneath the lower turbine, at a rate not exceeding 8 l/min. Samples taken over the course of cultivation (FIG. 1) indicate that pertussis toxin production closely parallels growth of the organism. Bacterial growth and pertussis toxin production reach a maximun in about 20 hours and do not significantly decline thereafter as shown in FIG. 1. These results demonstrate an efficient commercial level cultivation of *B. pertussis* by the method of the present invention.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for the enhanced production of a *Bordetella pertussis* toxin, which comprises the steps of:
   (a) charging a fermentor of a commercial scale capacity with a sterilized first medium, which is capable of supporting the growth of *Bordetella pertussis* and the production of a *Bordetella pertussis* toxin;
   (b) inoculating said first medium with a culture of *Bordetella pertussis* bacteria which has been grown in a second culture medium containing a growth promoting amount of an iron salt, to give a combined first and second medium having a concentration of iron which is equivalent to the concentration of iron in a solution containing about 1.0 mg/liter of $FeSO_4 \cdot 7 H_2O$; and
   (c) cultivating the *Bordetella pertussis* bacteria present in the combined mediums under agitated submerged culture conditions at about 36° C. in the presence of an antifoam agent and dissolved oxygen at about a 40% saturation level.

2. The method of claim 1, wherein the first medium contains no iron.

3. The method of claim 1, wherein the fermentor's capacity is about 100 liters.

4. The method of claim 1, wherein the iron salt is ferrous sulfate.

5. The method of claim 1, wherein said antifoam agent is polydimethylsiloxane.

6. The method of claim 1, wherein the dissolved oxygen at about 40% saturation level is achieved by introducing pure oxygen into the fermentor at a flow rate not exceeding about 8% of the fermentor's volume per minute.

* * * * *